United States Patent [19]

Fine

[11] Patent Number: 5,298,237
[45] Date of Patent: Mar. 29, 1994

[54] GEL COMPOSITION FOR REDUCTION OF GINGIVAL INFLAMMATION AND RETARDATION OF DENTAL PLAQUE

[75] Inventor: Daniel H. Fine, Leonia, N.J.

[73] Assignee: The Trustees of Columbia University in the City of New York, New York, N.Y.

[21] Appl. No.: 826,482

[22] Filed: Jan. 24, 1992

[51] Int. Cl.$^5$ .................. A61K 7/16; A61K 31/375; A61K 33/34
[52] U.S. Cl. .................. 424/49; 424/630; 424/638; 514/474; 514/900; 514/902; 514/944
[58] Field of Search .................. 424/49–58, 424/630, 638; 514/474, 944, 900, 902

[56] References Cited

U.S. PATENT DOCUMENTS

| | | |
|---|---|---|
| 2,470,906 | 5/1949 | Taylor . |
| 3,065,139 | 11/1962 | Ericsson et al. . |
| 3,886,265 | 5/1975 | Evers et al. . |
| 3,992,519 | 11/1976 | Hofmann et al. . |
| 4,332,791 | 6/1982 | Raaf, I et al. ............ 424/49 |
| 4,339,429 | 7/1982 | Raaf, II et al. ........... 424/49 |
| 4,622,220 | 11/1986 | Frosch, I .................. 424/49 |
| 4,652,444 | 3/1987 | Maurer, I .................. 424/49 |
| 4,708,864 | 11/1987 | Maurer, II ................. 424/49 |
| 4,719,100 | 1/1988 | Frosch, II ................. 424/49 |
| 4,795,628 | 1/1989 | Afseth ..................... 424/49 |
| 4,824,661 | 4/1989 | Wagner .................... 424/52 |
| 4,997,640 | 3/1991 | Bird et al. ................ 424/52 |
| 5,037,633 | 8/1991 | Ziemkiewicz et al. ....... 424/49 |
| 5,037,634 | 8/1991 | Williams et al. ........... 424/49 |
| 5,094,842 | 3/1992 | Riley ...................... 424/52 |

OTHER PUBLICATIONS

Barron, E. S. G., et al., Journal of Biological Chemistry, (1936), vol. 112, pp. 625–640 (Exhibit F).
Ball, E. G., Journal of Biological Chemistry, (1937), vol. 118, pp. 219–239 (Exhibit G).
Mystkowski, E. M., Biochemical Journal, (1942), vol. 36, pp. 494–500 (Exhibit H).
Ericsson, Y., Acta Pathologica Et Microbiologica Scandinavica, (1954), vol. 35, pp. 573–583.
Berghagen, N., et al. Svensk Tandlakare-Tidskrift (1954), vol. 47, pp. 409–418.
Ericsson, Y., Acta Pathologica Et Microbiologica Scandinavica (1955), vol. 37, pp. 493–506.
Ericsson, Y., Acta Pathologica Et Microbiologica Scandinavica, (1955), vol. 37, pp. 507–527.
Wade, A. B., et al. British Dental Journal, (1961), vol. III, pp. 280–285.
Muller, E., et al., Helvetica Odontologica Acta, (1962), vol. 6, pp. 42–45.
Kristoffersen, T., Odontologisk Tidskrift, (1963), vol. 71, pp. 179–198.
Johansen, J. R., et al., Acta Odontologica Scandinavica, (1970), vol. 28, No. 5, pp. 661–677.

*Primary Examiner*—Shep K. Rose
*Attorney, Agent, or Firm*—John P. White

[57] ABSTRACT

The present invention provides a gel composition useful for the prevention or treatment of gingivitis, periodontal disease, and dental plaque which comprises ascorbic acid, copper sulfate, and essentially no added oxidizing agent, in concentrations sufficient for the prevention or treatment of gingivitis, periodontal disease, and dental plaque; and a gel carrier. The invention also provides a method for the prevention or treatment of gingivitis, periodontal disease, and dental plaque in the oral cavity of a subject which comprises applying for an effective period of time within the oral cavity of a subject an amount of the gel composition effective to prevent or treat gingivitis, periodontal disease, and dental plaque.

11 Claims, No Drawings

GEL COMPOSITION FOR REDUCTION OF GINGIVAL INFLAMMATION AND RETARDATION OF DENTAL PLAQUE

BACKGROUND OF THE INVENTION

Throughout this application various patents and publications are referenced and citations are provided in parentheses. The disclosure of these patents and publications in their entireties are hereby incorporated by reference into this application in order to more fully describe the state of the art to which this invention pertains.

The presence of microorganisms is associated with gingivitis, periodontal disease, and dental plaque. That microorganisms are a causative element of, or are associated with, dental and other diseases is the underlying principle of many studies (See e.g., Ericsson, Y., Acta Pathol Microbiol. Scandinav., 35: 573-583 (Fasc 6), (1954); Ericsson, Y., and Lundbeck, H., Acta Pathol Microbiol. Scandinav., 37: 493-506 (Fasc. 6), (1955); Ericsson, Y., Lundbeck, H., Acta Pathol. Microbiol. Scandinav., 37: 507-526 (Fasc 6), (1955); Kristoffersen, T., Odont. Tid., 71: 179-198, (1963); and Johansen, J. R., Flotra, L., and Gjermo, P., Acta Odontol. Scandinav., 28: (5) 661-677, (1970)).

Studies have shown that copper ion has a catalytic effect on the oxidation of ascorbic acid (See, e.g., Ball, E. G., J. Biol. Chem , 118: 219-239, at 223 citing references, (1937); Barron, E.S.G., DeMeio, R. H., and Klemperer, F., J. Biol. Chem., 112: 625-640, (1936); Mystkowski, E. M., Biochem. J., 36: 494-500 (1942)).

Studies have also shown that the oxidation of ascorbic acid in the presence of the copper ion catalyst has antimicrobial effects, and that copper ion greatly enhanced those effects. (Ericsson, Y., Lundbeck, H., Acta Pathol. Microbiol. Scandinav., 37: 493-506 (Fasc. 6), (1955); Kristoffersen, T., Odont. Tid., 71: 179-198, 180 and citations therein, (1963)). In other words, these studies showed that copper ion has a synergistic effect on the antimicrobial properties of the ascorbic acid oxidation reaction.

Ericsson, S. Y., et al., U.S. Pat. No. 3,065,139 (1962), disclose an anti-infectant or antimicrobial composition that was clinically tested for gingivitis and stomatitis. The composition comprises an enediol compound such as ascorbic acid, an added oxidizing agent such as sodium percarbonate, and a catalyst such as copper ion. The patent discloses that the invention is in the form of a water-free powder, tablet, or paste, which at time of application is dissolved or suspend in water, making an aqueous solution Thus, upon application, the composition is in a water solution Ericsson et al. disclose that a clinically useful solution may at the moment of application contain about 1.76 mg/ml to 7.04 mg/ml ascorbic acid (or 0.01 to 0.04 molar concentration); 1 mg/ml to 5 mg/ml sodium percarbonate (or 0.1 to 0.5 weight percent); and about 0.008 mg/ml copper sulfate (or 0.0008 weight percent). Ericsson et al. disclose that the reaction is very rapid once the ingredients are in presence of water, with the antimicrobial action being valid for a reaction time of only five minutes.

Unlike the composition of U.S. Pat. No. 3,065,139, the gel composition of the present invention involves the use of a gel carrier, does not require an added oxidizing agent, and provides antimicrobial action effective for at least thirty minutes. Moreover, because of the gel carrier, the ascorbic acid and copper ion can be targeted to desired or affected areas of the oral cavity, and when released from the gel, the ascorbic acid and copper remain bound or stuck to the tooth surface. U.S. Pat. No. 3,065,139 does not disclose an unexpected improvement in the prevention or treatment of gingivitis, periodontal disease, or dental plaque by using a gel composition comprising ascorbic acid and copper ion.

Taylor, R., U.S. Pat. No. 2,470,906 (1949), discloses a composition useful for the cleansing of teeth, gums, tongue, and other parts of the oral cavity. The composition comprises ascorbic acid or its acid analogues in a liquid, paste, or powder form. The patent does not disclose or suggest the use of copper ion, a gel carrier, or use of the composition for the prevention or treatment of gingivitis, periodontal disease, and dental plaque.

Evers et al., U.S. Pat. No. 3,886,265 (1975), disclose a composition effective for bad breath. The composition comprises an enediol compound having at most six carbon atoms such as ascorbic acid, and a peroxide oxidizing agent. The patent does not disclose or suggest the use of copper ion, a gel carrier, or the use of the composition for the prevention or treatment of gingivitis, periodontal disease, or dental plaque. Also, the present invention contains no added oxidizing agent.

Hofmann et al., U.S. Pat. No. 3,992,519 (1976), disclose a composition in toothpaste, mouthwash, or chewing gum form comprising an antibacterial compound, a vitamin, and a surfactant, useful in the prophylaxis and treatment of inflammatory diseases of the periodontium such as gingivitis and periodontitis. The antibacterial component of the patent comprises one or more pharmaceutically acceptable esters of p-hydroxybenzoic acid and or one or more pharmaceutically acceptable esters of o-hydroxybenzoic acid. The vitamin component of the patent comprises one or more of the following: aescin, rutin, panthenol, nicotinamide and vitamin E, and may further comprise small amounts of other vitamins such as vitamin C, vitamin K, and B group vitamins. The surfactant component of the patent comprises one or more anionic surfactants from examples of a listed group, or cationic surfactants. The patent does not disclose or suggest the use of copper ion or a gel carrier. Moreover, although the composition may further comprise small amounts of vitamins such as vitamin C (ascorbic acid), Hofmann et al. do not disclose or suggest the use of vitamin C (ascorbic acid) as the primary vitamin component. Furthermore, the present invention does not require the use of either a surfactant or an added antibacterial component.

Two commercial products containing ascorbic acid, sodium percarbonate, and copper sulfate have been produced The first product appeared under the trade name Ascoxal ®, or Gum-Ox ®; and the second commercial product appeared under the trade name Ascoxal T ®. The manufacturer suggested that Ascoxal ® would be helpful in the treatment of stomatitis, gingivitis, and oral mycotic and coli-infections, among other uses. (Kristoffersen, T., Odont. Tid., 71: 179-198, 181, (1963)).

The compositions of Ascoxal ® and Ascoxal T ® are similar to that disclosed in U.S. Pat. No. 3,065,139, containing ascorbic acid, copper sulfate, and sodium percarbonate. Ascoxal ® contains 100 mg ascorbic acid, 70 mg sodium percarbonate, and 0.2 mg copper sulfate in tablet form, which is dissolved in 25 ml of water to provide a water solution taken as a mouthwash. (Johansen, J. R., Flotra, L., Gjermo, P., Acta Odontol. Scandinav., 28: (5) 661-677, 661-662 (1970). The resulting concentrations of ascorbic acid, copper sulfate, and sodium percarbonate of the Ascoxal ® mouthwash are approximately the same concentrations as disclosed by Ericsson in U.S. Pat. No. 3,065,139, and in Ericsson, Y., Acta Pathol. Microbiol. Scandinav , 35: 573-583 (Fasc. 6), (1954). Ascoxal T ® is in the form of a chewable tablet, containing a higher local concentration of the active components of the same ingredients present in the Ascoxal ® product. (Johansen, J. R., Flotra, L., and Gjermo, P., Acta Odontol. Scandinav., 28: (5) 661-677, 662, (1970)).

In contrast to Ascoxal ® and Ascoxal T ®, the present invention is in the form of a gel. Because the compositions of Ascoxal ® and Ascoxal T ® correspond to that described in U.S. Pat. No. 3,065,139, the oxidation reaction of ascorbic acid takes place within a short time after the ingredients are in the presence of water, with the antimicrobial action being valid for a time of only five minutes. The reaction in the present invention, however, is effective for at least thirty minutes. Furthermore, the present invention is designed to allow targeting to desired areas of the oral cavity. Another difference is that the composition of the Ascoxal ® and Ascoxal T ® products include sodium percarbonate as an oxidizing agent, whereas the present invention has no added oxidizing agent.

Researchers have clinically tested the Ascoxal ® mouthwash and the Ascoxal T ® chewable tablet products for their effectiveness in treating gingivitis and the prevention of plaque. Conflicting results were obtained. (Cf. Kristoffersen, T., Odont. Tid., 71: 179-198, (1963) (finding no statistically significant effect on Ascoxal ® use in rate and degree of plaque and calculus formation); Muller, E., Schroeder, H. E., and Muhlemann, H. R., Helv. Odont. Acta, 6: 42-45, 44 (1962) (finding that Ascoxal ® had marked inhibitory effect on early calculus formation)).

In a later study, Johansen et al. clinically evaluated Ascoxal T ® for its effect on plaque formation and gingivitis. (Johansen, J. R., Flotra, L., and Gjermo, P., Acta Odontol. Scandinav., 28: (5) 661-677, (1970)). Johansen et al. explained that the purpose of their study was to clarify the effects of Ascoxal T ® on plaque formation and gingivitis, noting conflicting results of previous investigations examining the use of Ascoxal ®. (Johansen, J. R., Flotra, L., and Gjermo, P., Acta Odontol. Scandinav., 28: (5) 661-677, 662 and citations therein, (1970)). In their study, Johansen et al. found no statistically significant effect on the progression of experimental gingivitis, and with regard to plaque formation, their results were inconclusive. (Johansen, J. R., Flotra, L., and Gjermo, P., Acta Odontol. Scandinav., 28: (5) 661-677, (1970)).

The present invention reveals a gel composition containing ascorbic acid and copper ion that optimizes the antimicrobial effect for the prevention or treatment of gingivitis, periodontal disease, and dental plaque. This invention differs from the prior art in three ways. First, the present invention requires that the ascorbic acid and copper ion be inside a gel carrier. In contrast, the prior art does not disclose or suggest a gel carrier. Secondly, in this invention the reaction between ascorbic acid and copper ion, upon application, will remain effective for at least thirty minutes. In contrast, the prior art, especially U.S. Pat. No. 3,065,139, and Ascoxal ® and the Ascoxal T ® which have compositions similar to U.S. Pat. No. 3,065,139, does not suggest that the reaction will be effective for at least thirty minutes. Thirdly, this invention requires the addition of no oxidizing agent. In contrast, U.S. Pat. No. 3,065,139, Ascoxal ®, and Ascoxal T ® require the addition of an oxidizing agent, such as sodium percarbonate.

The gel composition of the present invention has important advantages over liquid, chewable tablet, or paste forms. One important advantage is the property of substantivity. Substantivity relates to the ability to bind or stick to a surface. Specifically, substantivity here relates the ability of the ascorbic acid and copper ion to bind or stick to the tooth surface, upon release from the gel composition upon application within the oral cavity of a subject. Substantivity is important because it allows for longer contact of the ascorbic acid and copper ion with the tooth surface. The result is enhancement of the antimicrobial effect against the significant oral microorganisms that are causative agents of, or associated with, various dental diseases, including gingivitis, periodontal disease, and dental plaque.

Experiments using atomic absorption showed that application of the gel composition to enamel leaves the copper ion stuck or bound to the enamel surface where the gel was applied. Although the amount of ascorbic acid remaining stuck or bound to the tooth surface when released from the gel composition was not measured, it is believed that the ascorbic acid likewise remains stuck or bound to the tooth surface as well.

In contrast, experiments using atomic absorption showed that when the ascorbic acid and copper ion are delivered in aqueous form, as in a mouthwash, there is substantially less sticking or binding of copper ion to the tooth surface. In other words, the gel composition of this invention increases the contact time of the copper ion, and presumably the ascorbic acid, with tooth surfaces.

In practice, upon application of the gel composition, the patient is instructed not to rinse the mouth until about thirty minutes after application of the gel composition. The antimicrobial activity continues throughout this thirty minute period, for Barron, et al. noted that in experiments involving an aqueous solution of 0.02 mM of ascorbic acid in phosphate buffer plus 0.1 molar NaCl, with 0.0002 mM of copper chloride as catalyst, with final pH of 6.00, half of the ascorbic acid was oxidized in 16.2 minutes; and that without NaCl, ascorbic acid was half oxidized in 15 minutes. (Barron, E.S.G., DeMeio, R. H., and Klemperer, F., J. Biol. Chem., 112: 625-640, 639 (1936).

The gel also allows for targeting of the ascorbic acid and copper ion to desired areas of the oral cavity Targeting is especially useful for treatment purposes, allowing the gel to be applied to affected areas. The targeting and substantivity properties of the gel thus allow for application to desired areas of the oral cavity, and prolonged contact of the ascorbic acid and copper ion to exert the antimicrobial effect. In contrast, mouthwashes or chewable tablets allow for only momentary contact of the ascorbic acid and copper ion with teeth, and do not practically allow for targeting. This invention significantly overcomes those problems.

Another important feature of this invention is non-toxicity. This invention is to be applied to tooth or gum surfaces within the oral cavity of a subject for the prevention or treatment of gingivitis, periodontal disease, and dental plaque. This invention involves the application of non-toxic agents. Since the diseases are chronic in nature, treatment might cover long periods of times, ranging from days, months, to years. The active agents, namely ascorbic acid and copper ion, are vitamins and minerals.

In contrast, the presence of sodium percarbonate in the composition described in U.S. Pat. No. 3,065,139, which in turn is similar to the compositions of Ascoxal ®, and Ascoxal T ®, leads to questions of safety. In that regard, Muller et al., in a clinical evaluation finding that Ascoxal ® had a marked inhibitory effect on early calculus formation, noted that the inhibitory data observed with Ascoxal ® rinsing are only of theoretical interest, saying that adverse effects on the oral flora and mucosa are possible after its use for years as an oral antiseptic. (Muller, E., Schroeder, H. E., and Muhlemann, H. R., Helv. Odont. Acta, 6: 42–45, 44 (1962). Ericsson, in a study involving a composition similar to the one described in U.S. Pat. No. 3,065,139, Ascoxal ®, and Ascoxal T ®, said that the possibility of local or general effects attending the application of ascorbic acid with an oxidizing agent to the mucous membranes of the body should not be disregarded, calling for careful study. (Ericsson, Y., Acta Pathol. Microbiol. Scandinav., 35: 573–583, 582 (1954).

SUMMARY OF THE INVENTION

The present invention provides a gel composition useful for the prevention or treatment of gingivitis, periodontal disease, and dental plaque which comprises ascorbic acid, copper sulfate, and essentially no added oxidizing agent, in concentrations sufficient for the prevention or treatment of gingivitis, periodontal disease, and dental plaque; and a gel carrier.

The invention also provides a method for the prevention or treatment of gingivitis, periodontal disease, and dental plaque in the oral cavity of a subject which comprises applying for an effective period of time within the oral cavity of a subject an amount of the gel composition effective to prevent or treat gingivitis, periodontal disease, and dental plaque.

DETAILED DESCRIPTION OF THE INVENTION

The present invention provides a gel composition useful for the prevention or treatment of gingivitis, periodontal disease, and dental plaque which comprises ascorbic acid, copper sulfate, and essentially no added oxidizing agent, in concentrations sufficient for the prevention or treatment of gingivitis, periodontal disease, and dental plaque; and a gel carrier.

The copper ion acts catalytically. Therefore, relative to the concentration of ascorbic acid, the concentrations of copper sulfate is smaller. In the preferred embodiment, the concentration of copper sulfate is from about 0.05 mg/ml to about 1 mg/ml; and the concentration of ascorbic acid is from about 0.5 mg/ml to about 75 mg/ml.

Because it is the copper (2+) ion that catalyzes the oxidation reaction of ascorbic acid, copper sulfate may be substituted by other copper salts, so long as the copper salt is chosen from a group of any copper salts that are soluble in the composition, yielding the copper (2+) ion, and further will not adversely interfere with the reaction between ascorbic acid and copper ion, or otherwise make the composition ineffective for the prevention or treatment of gingivitis, periodontal disease, and dental plaque. Additionally, the copper salt must be non-toxic in the amounts used.

The concentrations of ascorbic acid and copper ion within the gel may vary depending on whether the invention is used for prevention or treatment purposes, and depending upon the dental disease being treated. Generally, the concentrations of ascorbic acid and copper ion will be greater for treatment than for preventative purposes. For example, for preventative purposes, the preferred concentrations of ascorbic acid and copper ion may be as low as about 0.5 mg/ml and about 0.05 mg/ml, respectively. In contrast, for treatment purposes, the preferred concentrations of ascorbic acid and copper ion may be as high as about 75 mg/ml and about 1 mg/ml, respectively.

The gel carriers suitable for use in the present invention include any of those gels that allow for the release of a sufficient amount of copper ion and ascorbic acid in the desired amount of time, and which further provide the desired amount of substantivity of ascorbic acid and copper ion, and which further do not adversely interfere with the reaction between ascorbic acid and copper ion, or otherwise make the gel composition ineffective for the prevention or treatment of gingivitis, periodontal disease, and dental plaque. Such gel carriers may include, but are not limited to, gelatin, polyethylene glycol, guar gum, or combinations thereof. Other gel carriers with the above described properties may be used. Polyethylene glycols of average molecular weights ranging from about 600 to about 4000 are preferred. Preferably, the gel carrier comprises gelatin and polyethylene glycol, wherein the concentration of gelatin ranges from about 20 mg/ml to about 40 mg/ml, and the concentration of polyethylene glycol ranges from about 400 mg/ml to about 475 mg/ml. Guar gum might be added to gelatin to stabilize the gelatin.

In the preferred embodiment, the ascorbic acid and copper sulfate are kept in separate gel carriers until time of application to prevent premature reaction of the ascorbic acid and copper ion. A particularly effective gel composition is to have ascorbic acid in a gel carrier of gelatin, and copper ion in a gel carrier of polyethylene glycol. The two gel carriers are mixed just before application. Upon application, release of the ascorbic acid and copper ion from the gel composition is quick, ranging from about less than one minute to about thirty minutes.

In the preferred embodiment, ascorbic acid at a concentration from about 1 mg/ml to about 150 mg/ml in a gel carrier comprising gelatin in a concentration from about 40 mg/ml to about 80 mg/ml, and copper sulfate at a concentration from about 0.1 mg/ml to about 2 mg/ml in a gel carrier comprising polyethylene glycol of molecular weights between 600 to 4000 in a concentration from about 800 mg/ml to about 950 mg/ml, provide optimum ascorbic acid and copper ion release when the two gel carriers are mixed at time of application.

The gel composition may further comprise a suitable amount of buffer, so long as the buffer does not adversely interfere with the reaction between ascorbic acid and copper ion, or otherwise make the gel composition ineffective for the prevention or treatment of gingivitis, periodontal disease, and dental plaque. Additionally, the buffer must be non-toxic in the amounts used. The pH may be maintained at a range of from about 5.8 to about 7.0. Potassium hydroxide may be added to adjust the pH to the appropriate value.

In the preferred embodiment, the buffer is potassium phosphate, which is used to maintain the pH at about 6.5. The amount of potassium phosphate in the preferred embodiment ranges from about 0.05 mg/ml to about 15 mg/ml. Potassium hydroxide may be added, if necessary, to adjust the pH to 6.5.

The gel composition may further comprise one or more preservatives, so long as those additional components do not adversely interfere with the reaction between ascorbic acid and copper ion, or otherwise make the gel composition ineffective for the prevention or treatment of gingivitis, periodontal disease, and dental plaque. Additionally, the preservative must be non-toxic in the amounts used.

Possible preservatives include, but are not limited to, methylparaben, propylparaben, or combinations thereof. In the preferred embodiment, the gel composition comprises methylparaben at a concentration from about 1 mg/ml to about 25 mg/ml and propylparaben at a concentration from about 0.1 mg/ml to about 10 mg/ml. Experiments have shown a slight enhancement to the antimicrobial activity due to the addition of methylparaben and propylparaben at the recommended concentrations.

The gel composition may further comprise a taste agent. A taste agent may be used, so long as the taste agent will not adversely interfere with the reaction between ascorbic acid and copper ion, or otherwise make the gel composition ineffective for the prevention or treatment of gingivitis, periodontal disease, and dental plaque. Additionally, the taste agent must be non-toxic in the amounts used.

The most preferred gel compositions are given the following table. The most preferred embodiment comprises two separate gel carriers which are combined at time of application. The gel compositions are made by mixing the two gel carriers in equal amounts:

| CHEMICAL COMPOUND | CONCENTRATION (mg/ml) | PREFERRED CONCENTRATION RANGE (mg/ml) |
| --- | --- | --- |
| GEL CARRIER (A) | | |
| (1) Ascorbic Acid | 100 | 1-150 |
| (2) Gelatin | 80 | 40-80 |
| (3) Methylparaben | 10 | 1-25 |
| (4) Propylparaben | 1 | 0.1-10 |
| (5) Potassium Phosphate | 10 | 1-30 |
| (6) Potassium Hydroxide | to bring to pH 6.5 | |
| GEL CARRIER (B) | | |
| (1) Copper Sulfate | 0.4 | 0.1-2 |
| (2) Polyethylene Glycol 600-4000 | 950 | 800-950 |
| (3) Methylparaben | 10 | 1-25 |
| (4) Propylparaben | 1 | 0.1-10 |

One method of preparing the gel composition is as follows. The method may vary depending upon the gel carrier or other chemicals used, quantity to be prepared, method of application, and other factors. Chemicals 1, 3, and 4 are added to distilled water that is heated if necessary to aid dissolution. For Gel Carrier (A), the pH is measured at room temperature; chemical 5, is added if necessary to bring the pH to about 6.5; chemical 6, or some other appropriate base, is added along with the buffer if necessary to adjust the pH to about 6.5. The solution is then heated to about 195° F. and the gel carrier, chemical 2, is added while stirring to yield a homogenous gel after cooling to room temperature. Other methods of preparation may be used, so long as the resulting gel composition is effective for the prevention or treatment of gingivitis, periodontal disease, and dental plaque. In the preferred embodiment, under storage conditions, it is desirable to keep the ascorbic acid containing gel carrier under oxygen-free (anaerobic) conditions, in order to maintain the activity of the ascorbic acid. That can be done by a variety of suitable packaging procedures.

The present invention also provides a method for the prevention or treatment of gingivitis, periodontal disease, and dental plaque in the oral cavity of a subject which comprises applying within the oral cavity of a subject an amount of the gel composition effective to prevent or treat gingivitis, periodontal disease, and dental plaque.

The gel composition is applied to the desired areas of the tooth or gum surfaces within the oral cavity of the subject. The gel is designed so that the release of the ascorbic acid and copper ion upon application of the gel composition is quick, ranging from about less than one minute to about thirty minutes. After application of the gel, the subject expectorates the gel substance, or alternatively, the gel dissolves. The subject does not rinse out the mouth for at least thirty minutes. The ascorbic acid and copper ion released from the gel composition thus remain within the oral cavity for about thirty minutes.

The amount of gel applied depends upon whether the gel composition is to be used for preventative or treatment purposes, the dental disease, patient peculiarities, and other factors. Treatment schedules may cover a wide period, ranging from days to months to years, depending upon the above factors.

Certain preferred embodiments of the invention are set forth in the Experimental Details section which follows. This section is provided to aid in an understanding of the invention but is not intended to, and should not be construed to, limit in any way the invention as set forth in the claims which follow thereafter.

EXPERIMENTAL DETAILS

Chemical reagents are obtained at various chemical supply companies, such as Sigma Chemical Company, St. Louis, Missouri; and Aldrich Chemical Company, Milwaukee, Wisconsin.

Experiment One

Synergistic Effect of Copper With Ascorbic Acid

Experiment One demonstrates the synergistic effect of copper ion with ascorbic acid. Ascorbic acid and copper ion independently have a rather modest effect on pioneer colonizers of the tooth surface, namely Streptococcal and Actinomyces species. But in combination, ascorbic acid and copper ion have a pronounced synergistic effect.

Thus, an aqueous solution of 40 mg/ml of copper sulfate without ascorbic acid is required to kill an inoculum of *Streptococcus sanguis* (optical density =0.50), and an aqueous solution of 20 mg/ml of ascorbic acid without copper sulfate is required. But, when 10 mg of ascorbic acid is combined with 2 mg of copper sulfate in 100 milliliters of solution, the solution can be diluted 128 times to attain comparable results in attaining kill, making the final concentration of ascorbic acid 0.07813 mg/ml and that of copper sulfate 0.01563 mg/ml. Another experiment showed that holding concentration of ascorbic acid constant at 10 mg/ml allowed the concentration of copper sulfate to be lowered to 1 μg/ml (0.001 mg/ml) to achieve the desired killing of *Strepto-*

*coccus sanguis*. Similar synergistic effects were achieved when this combination was tested against Actinomyces species. This combination was chosen from a large list of vitamins, minerals and amino acids tested in vitro against a broad range of oral bacteria.

The following tables summarize the results.

TABLE I

Minimum Inhibitory Concentration Summary; In Aqueous Solution (dose to kill indicated microorganism in twenty four hours; units are mg/ml)

| | Microorganism | | |
|---|---|---|---|
| Agent | Capnocyt. | A. A. | A. Naesl. |
| Vitamin B | 20 | 40 | 20 |
| Vitamin C | 40 | 20 | 10 |
| Vitamin U | 80 | 80 | 80 |
| Copper Sulfate | 1 | 0.06 | 0.06 |
| Zinc Lactate | 1 | 0.1 | 0.1 |
| Glycine | 30 | 20 | 20 |
| D-Methionine | 30 | 20 | 20 |
| D-Arginine | 80 | 20 | 20 |
| D-Threonine | 80 | 10 | 20 |

| | Microorganism | | |
|---|---|---|---|
| Agent | S. Sanguis | S. Mutans | A. Viscosus |
| Vitamin B | 40 | 40 | 10 |
| Vitamin C | 5 | 10 | 20 |
| Vitamin U | 80 | 80 | 80 |
| Copper Sulfate | 80 | 80 | 0.06 |
| Zinc Lactate | 80 | 80 | 0.13 |
| Glycine | 20 | 40 | 20 |
| D-Methionine | 30 | 20 | 20 |
| D-Arginine | 20 | 40 | 40 |
| D-Threonine | 30 | 40 | 40 |

In Table I above, Capnocyt. is Capnocytophaga; A. A. is *actinobacillus actinomycetemcomitans;* A. Naesl. is *Actinomycetes naeslundii;* S. Sanguis is *Streptococcus sanguis;* S. Mutans is *Streptococcus mutans;* and A. Viscosus is *Actinomycetes viscosus*.

Experiments in Table I were performed in aqueous solution. Table I shows that, individually, ascorbic acid (vitamin C) and copper sulfate required smaller doses to kill microorganisms. On that basis, it was decided to test the effects of ascorbic acid and copper sulfate together.

TABLE II

Synergism of Copper Sulfate and Ascorbic Acid In Aqueous Solution

| Combination Tested | | | MIC vs. S. Sanguis |
|---|---|---|---|
| Copper Sulfate | = | 1 mg/ml | 1/1024 dilution |
| Ascorbic Acid | = | 40 mg/ml | |
| Preservatives | | | |
| Copper Sulfate | = | 1 mg/ml | 1/512 dilution |
| Ascorbate | = | 40 mg/ml | |
| Copper Sulfate | = | 1 mg/ml | 1/32 dilution |
| Salicylic Acid | = | 40 mg/ml | |
| Preservatives | | | |
| Copper Sulfate | = | 1 mg/ml | 1/16 dilution |
| Salicylic Acid | = | 40 mg/ml | |

In Table II above, MIC is Minimum Inhibitory Concentration (dose to kill indicated microorganism in twenty four hours); S. Sanguis is *Streptococcus Sanguis;* Preservatives consists of methylparaben at 10 mg/ml and propylparaben at 1 mg/ml.

Experiment Two

Test of Various Gels

A series of gel carriers were tested for their ability to allow for total release of the ascorbic acid and copper ion. Three gels were tested for release at 24 hours and at 30 minutes. The gels tested included: carboxymethyl cellulose; gelatin; and a group of agars and gums consisting of gum arabic, gum tragacanth and agar-agar.

In the 24 hour test, carboxymethyl cellulose performed best, and thus 10 mg/ml of ascorbic acid and 0.050 mg/ml of copper sulfate was sufficient to kill the test organisms. In the 24 hour experiment, the gelatin performed as well, but was totally dissolved in the test media. The gums consisting of gum arabic, gum tragacanth and agar-agar performed least well, and thus over 0.2 mg/ml of copper sulfate was needed to kill. However, in the ten minute experiment, only the gelatin released sufficient amount of ascorbic acid and copper ion to achieve the desired effect.

Since the subject will be instructed not to rinse the mouth for about thirty minutes upon application of the gel composition within the oral cavity, then, from the group of gel carriers tested, gelatin was found to have desirable properties. In this experiment, gelatin with a concentration range from about 40 mg/ml to about 80 mg/ml provides the proper consistency and viscosity needed.

Experiment Three

In vitro Antimicrobial Activity of Gel Composition Against Significant Oral Microorganisms:

The antimicrobial activity of the gel composition was tested in vitro against the following significant oral microorganisms:
1. Actinobacillus actinomycetemcomitans
2. Capnocytophaga gingivalis
3. Actinomycetes viscosus
4. Actinomycetes naeslundii
5. Streptococcus sanguis
6. Streptococcus mutans
7. Bacteroides gingivalis
8. Bacteroides intermedius
9. Bacteroides oralis
10. Bacteroides oris
11. Veillonella parvula
12. Fusobacterium nucleatum
13. Wolinella recta
14. Eikenella corrodens 100% kill of the above tested microorganisms was obtained after ten minute exposure to the gel composition. The gel composition is obtained by mixing equal amounts of Gel Carrier (A) and Gel Carrier (B), defined as follows. Gel Carrier (A) comprises 100 mg/ml ascorbic acid, 80 mg/ml gelatin, 10 mg/ml methylparaben, 1 mg/ml propylparaben, 10 mg/ml phosphate buffer, and potassium hydroxide, if necessary, to adjust pH to about 6.5. Gel Carrier (B) comprises 0.4 mg/ml copper sulfate, 950 mg/ml polyethylene glycol 1000, 10 mg/ml methylparaben, and 1 mg/ml propylparaben.

Experiment Four

Effect of Gels on Enamel Binding of Bacteria

The first part of this experiment involves testing the binding of bacteria to enamel when the copper ion and ascorbic acid are in an aqueous solution. The second part of this experiment involves testing the binding of bacteria to enamel when the copper ion and ascorbic acid are in a gel carrier. This experiment showed that the binding of bacteria to enamel is decreased when the copper ion and ascorbic acid are in a gel carrier, as opposed to being in an aqueous solution.

The theory behind the 3H-thymidine experiment is that the greater the substantivity (binding, or sticking) of the ascorbic acid and copper ion to the enamel surface, the fewer microorganisms will be bound to the enamel surface. The purpose is to compare the amount of binding, or sticking, of ascorbic acid and copper ion on the enamel surface when the ascorbic acid and copper ion are brought into contact with the enamel surface in an aqueous solution versus the gel composition. It was found that while an aqueous solution of ascorbic acid and copper ion was effective in the in vitro tube dilution assay, the aqueous solution produced poor results in a substantivity (binding, or sticking) assay. In this assay a culture of *Streptococcus sanguis* was radiolabeled with 3H-thymidine and grown to mid-logarithmic state overnight. Two hundred microliters of a radiolabeled suspension of bacteria were added to 4mm×3mm segments of enamel and incubated for sixty minutes at room temperature. Segments were washed and demineralized to remove bound bacteria and solutions were counted to determine the quantity of enamel bound bacteria. Experimental enamel segments were pre-incubated with either ascorbic acid, copper sulfate, the combination of ascorbic acid and copper sulfate, and water, which is the control.

Although an aqueous solution of the combination of copper and ascorbic acid once again was effective in killing a large percentage of the bacterial suspension added, no differences in enamel binding of these bacteria was seen when the control segments were compared to either ascorbic acid or ascorbic acid plus copper sulfate treated segments. A slight reduction in binding was seen in the copper sulfate treated segments.

Next, the 3H-thymidine experiment was performed to test the substantivity of ascorbic acid and copper ion when released from a gel composition. But first, a series of studies were undertaken to determine the best combination of gel carriers that would provide sufficient release of ascorbic acid and copper ion. This was done because it is believed that the more efficient the release from the gel, the greater the likelihood that the substantivity of ascorbic acid and copper ion will be enhanced. Initial experiments tested the killing effects of agents suspended in a variety of gels. The best release was obtained by combining equal amounts of two gel carriers of the following compositions, one gel carrier containing the ascorbic acid, and the other gel carrier containing the copper ion: 100 mg/ml ascorbic acid buffered with phosphate in 80 mg/ml gelatin, in combination with 0.4 mg/ml copper sulfate in 950 mg/ml Polyethylene Glycol 1000. This combination produced 90% kill of *Streptococcus sanguis* ten minutes after exposure, and 100% kill twenty minutes after exposure. No other combination tested produced equivalent results, although 100 mg/ml ascorbic acid in 80 mg/ml gelatin, plus 0.4 mg/ml copper sulfate in 80 mg/ml gelatin produced 100% kill thirty minutes after exposure.

The gel composition made by mixing the gelation gel carrier containing ascorbic acid with the Polyethylene Glycol 1000 gel carrier containing copper sulfate also provided a 5 fold reduction in *Streptococcus sanguis* binding to enamel in the in vitro 3H-thymidine assay. Thus fewer than 40 cells/mm2 were bound to enamel pre-incubated with the combination of ascorbic acid and copper sulfate while over 200 cells/mm2 were bound in the gelatin (control) treated segments. The ascorbic acid containing gel or the copper sulfate containing gel when used alone had results similar to the gelatin control.

Experiment Five

Substantivity of Copper

An atomic absorption experiment was performed to compare the amount of copper stuck or bound to enamel when the copper ion is brought into contact with enamel, first by contact with only an aqueous solution containing the ascorbic acid and copper ion, and secondly by contact with the gel composition. The gel composition was obtained by mixing equal amounts of two gels of the following compositions, one containing the ascorbic acid, and the other containing the copper ion: 100 mg/ml ascorbic acid buffered with phosphate in 80 mg/ml gelatin, in combination with 0.4 mg/ml copper sulfate in 950 mg/ml Polyethylene Glycol 1000. In this experiment, saliva coated enamel was exposed to reactants for ten minutes.

Results were obtained for a control, enamel exposed to an aqueous solution of ascorbic acid and copper, and enamel to which the gel combination was applied. The results of the atomic absorption experiment showed a substantial amount of copper remaining stuck or bound to the enamel surface when the gel composition was applied to the enamel, as opposed to when the enamel was in contact only with the aqueous solution of ascorbic acid and copper sulfate. The amount of copper remaining on the enamel when delivered by the aqueous solution is only slightly greater than for the control. Although only the copper can be measured by atomic absorption, the assumption is that the ascorbic acid is bound as well.

| The results of the atomic absorption experiment are as follows: | |
| --- | --- |
| Gel Combination, mean: | $0.112 \pm 0.020$ μg/ml |
| Aqueous System, mean: | $0.017 \pm 0.003$ μg/ml |
| Control, mean: | $0.012 \pm 0.00$ μg/ml |
| ANOVA analysis: | F value: 39.609; |
|  | p value: 0.0023 |
| Scheffe F test: | |
| Control vs. Aqueous: | 0.041 |
| Control vs. Gel Comb.: | 18.594, a 95% significance level |
| Aqueous vs. Gel Comb.: | 33.787, a 95% significance level |

Experiment Six

Clinical Evaluation

The purpose of the clinical evaluation was to determine the efficacy of the gel combination on the retardation of plaque development in a no-brushing experimental gingivitis protocol. The gel combination was obtained by mixing equal amounts, at time of application, of two gel carriers of the following compositions, one gel carrier containing the ascorbic acid, and the other gel carrier containing copper sulfate: 100 mg/ml ascorbic acid buffered with phosphate in 80 mg/ml gelatin, in combination with 0.4 mg/ml copper sulfate in 950 mg/ml Polyethylene Glycol 1000.

The results presented were obtained in a series of one week crossover experiments in which the gel combination containing ascorbic acid and copper ion was applied for one minute in a soft acrylic mouth guard to the gingival margin. In one portion of the crossover, the patient received the two gels without the ascorbic acid and copper sulfate whereas in the second crossover, the ascorbic acid and copper sulfate were placed in the gels.

The anti-plaque study was designed to allow patients to apply the active gel composition containing the ascorbic acid and copper sulfate, or a placebo gel, twice a day for one week without any other form of oral hygiene. Plaque was completely removed at start; each patient received either the active gel composition or placebo, which was applied for one week; plaque was scored; two week rest period followed; plaque was removed again; patients who received the placebo during the first week of application now received the gel combination, and visa versa, for one week; plaque was scored. The gel composition or placebo was applied using a custom made mouth guard, to ensure uniformity of application. The plaque was detected using Erythrosin stain. Plaque reduction was estimated by a Modified Loe-Silness Plaque Index.

Patients:
Seven patients, two groups:
  a) Group 1 placebo gel
  b) Group 2 active gel
Crossover Design:
  a) Patients use one gel (placebo) for one week;
  b) Patients rest for two weeks;
  c) Patients use other gel (active) for one week.
Execution:
  a) At start, patients receive prophy, instructions and gel (either placebo or active).
  b) Patients apply gel in tray under supervision. Gel applied twice a day during week and at home on the weekend.
  c) After first week, patient returns for examination and plaque scoring.
  d) Two week rest period.
  e) Patients return for a second prophy and is given second gel combination for application to complete crossover.
  f) Patient return for final examination, plaque scoring and prophy.

Results:
Active: $X=1.64 \pm 0.27$
Control: $X=2.24 \pm 0.12$

In the first series of experiments, it was discovered that the gel composition lost 30% of its in-vitro activity after completion of the one week period of experimentation. The gel stability problems were overcome in the laboratory and a second non-brushing, anti-plaque experiment was performed using the same subjects as in the first series of experiments. Results of these experiments indicated a further reduction of plaque by about 10% above the first result. Total plaque reduction as estimated by a Modified Loe-Silness Plaque Index was about 30% in the original experiment and about 40% after the improved gel preparation. However, visually, as can be seen in photographs, the amount of total plaque reduction appears to be greater than that reflected by the clinical plaque score. It is estimated that the actual plaque reduction would be approximately 90% if plaque weight was used to quantitate plaque reduction.

What is claimed is:

1. A gel composition useful for the prevention or treatment of gingivitis, periodontal disease, and dental plaque consisting essentially of (a) a gel carrier, and (b) ascorbic acid and copper sulfate, and essentially no oxidizing agent, in concentrations sufficient for the prevention or treatment of gingivitis, periodontal disease, and dental plaque, with the proviso that the gel composition comprises both ascorbic acid and copper sulfate no earlier than just prior to the application thereof said ascorbic acid and copper sulfate being kept in separate gel carriers until time of application to prevent premature reaction of the ascorbic acid and copper sulfate, the two gel carriers being mixed just before application, each gel carrier containing a buffer effective to maintain a pH of from about 5.8 to about 7.0.

2. The composition of claim 1 wherein the concentration of ascorbic acid is from about 0.5 mg/ml to about 150 mg/ml.

3. The composition of claim 1 wherein the concentration of copper sulfate is from about 0.1 mg/ml to about 2 mg/ml.

4. The composition of claim 1 wherein the gel carrier comprises gelatin, polyethylene glycol, guar gum, or combinations thereof.

5. The composition of claim 1 wherein the gel carrier comprises gelatin and polyethylene glycol.

6. The composition of claim 5 wherein the concentration of gelatin is from about 20 mg/ml to about 40 mg/ml, and the concentration of polyethylene glycol is from about 400 mg/ml to about 475 mg/ml.

7. The composition of claim which further comprises a suitable amount of buffer.

8. The composition of claim 7 wherein the buffer is potassium phosphate.

9. The composition of claim 1 which further comprises one or more preservatives.

10. The composition of claim 9 wherein the preservative is methylparaben, propylparaben, or combinations thereof.

11. A method for the prevention or treatment of gingivitis, periodontal disease, and dental plaque in the oral cavity of a subject which comprises applying for an effective period of time within the oral cavity of a subject an amount of the gel composition of claim 1 effective to prevent or treat gingivitis, periodontal disease, and dental plaque.

* * * * *